(12) United States Patent
Yang et al.

(10) Patent No.: US 9,402,710 B2
(45) Date of Patent: Aug. 2, 2016

(54) MACROPOROUS 3-D SCAFFOLDS FOR TISSUE ENGINEERING

(71) Applicant: The Board of Trustees for the Leland Stanford Junior University, Stanford, CA (US)

(72) Inventors: Fan Yang, Palo Alto, CA (US); Li-Hsin Han, Palo Alto, CA (US); Xinming Tong, Palo Alto, CA (US)

(73) Assignee: THE BOARD OF TRUSTEES FOR THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 13/943,738

(22) Filed: Jul. 16, 2013

(65) Prior Publication Data
US 2014/0017284 A1 Jan. 16, 2014

Related U.S. Application Data

(60) Provisional application No. 61/672,038, filed on Jul. 16, 2012.

(51) Int. Cl.
| | |
|---|---|
| C12N 5/00 | (2006.01) |
| C12N 11/08 | (2006.01) |
| A61L 27/38 | (2006.01) |
| A61L 27/52 | (2006.01) |
| A61F 2/02 | (2006.01) |
| A61K 35/12 | (2015.01) |
| A61K 35/35 | (2015.01) |
| A61K 9/00 | (2006.01) |

(52) U.S. Cl.
CPC . *A61F 2/02* (2013.01); *A61K 35/12* (2013.01); *A61K 35/35* (2013.01); *A61K 9/0024* (2013.01)

(58) Field of Classification Search
CPC .... C12N 5/0012; C12N 5/0062; C12N 11/08; A61L 27/38; A61L 27/52
See application file for complete search history.

(56) References Cited

U.S. PATENT DOCUMENTS

| | | | | |
|---|---|---|---|---|
| 5,158,881 A | * | 10/1992 | Aebischer | A61F 2/022 425/382 R |
| 5,283,187 A | * | 2/1994 | Aebischer | A61F 2/022 435/179 |
| 7,201,917 B2 | | 4/2007 | Malaviya et al. | |
| 7,531,503 B2 | | 5/2009 | Atala et al. | |
| 7,625,580 B1 | * | 12/2009 | Langer et al. | 424/426 |
| 7,854,923 B2 | | 12/2010 | Chen et al. | |
| 7,928,069 B2 | | 4/2011 | Prestwich et al. | |
| 2004/0028655 A1 | * | 2/2004 | Nelson | D06M 16/00 424/93.2 |
| 2009/0035855 A1 | * | 2/2009 | Ying | A61L 27/3633 435/377 |
| 2009/0069825 A1 | * | 3/2009 | Ying | A61L 27/26 606/151 |
| 2009/0258051 A1 | | 10/2009 | Chidambaram et al. | |
| 2011/0081417 A1 | * | 4/2011 | Sargeant | A61L 27/20 424/488 |
| 2011/0293669 A1 | * | 12/2011 | Bennett | A61K 9/06 424/400 |
| 2011/0293685 A1 | * | 12/2011 | Kuo | A61L 27/3604 424/422 |

OTHER PUBLICATIONS

Tuzlakoglu, Kadriye, et al. "Production and characterization of chitosan fibers and 3-D fiber mesh scaffolds for tissue engineering applications." Macromolecular Bioscience 4.8 (2004): 811-819.*
Nelson, Kevin D., et al. "Technique paper for wet-spinning poly (L-lactic acid) and poly (DL-lactide-co-glycolide) monofilament fibers." Tissue engineering 9.6 (2003): 1323-1330.*
Phelps, Edward A., et al. "Maleimide cross-linked bioactive PEG hydrogel exhibits improved reaction kinetics and cross-linking for cell encapsulation and in situ delivery." Advanced materials 24.1 (2012): 64-70.*
Zhu, Junmin. "Bioactive modification of poly (ethylene glycol) hydrogels for tissue engineering." Biomaterials 31.17 (2010): 4639-4656.*
Han, Li-Hsin, et al. "Microribbon-Like Elastomers for Fabricating Macroporous and Highly Flexible Scaffolds that Support Cell Proliferation in 3D." Advanced Functional Materials 23.3 (2013): 346-358.*
Han, Li- Hsin, Xinming Tong, and Fan Yang. "Photo-crosslinkable PEG-Based Microribbons for Forming 3D Macroporous Scaffolds with Decoupled Niche Properties." Advanced Materials 26.11 (2014): 1757-1762.*
Han, Li- Hsin, et al. "Microribbon-Like Elastomers for Fabricating Macroporous and Highly Flexible Scaffolds that Support Cell Proliferation in 3D." Advanced Functional Materials 23.3 (published online Sep. 4, 2012): 346-358.*
"Methoxy PEG Succinimidyl Succinamide." JenKem Technology USA. http://www.jenkemusa.com/product/methoxy-peg-succinimidyl-succinamide (accessed Mar. 9, 2016).*
"Amine reactive Crosslinker Chemistry." ThermoFisher Scientific. https://www.thermofisher.com/us/en/home/life-science/protein-biology/protein-biology-learning-center/protein-biology-resource-library/pierce-protein-methods/amine-reactive-crosslinker-chemistry.html (accessed Mar. 9, 2016).*
Barnes et al., "Feasibility of Electrospinning the Globular Proteins Hemoglobin and Myoglobin," J. Engineered Fibers and Fabrics, 2006, 1(2), pp. 16-29.

* cited by examiner

*Primary Examiner* — Bethany Barham
*Assistant Examiner* — Peter Anthopolos
(74) *Attorney, Agent, or Firm* — Knobbe, Martens, Olson & Bear, LLP

(57) ABSTRACT

Macroporous 3-D tissue engineering scaffold comprising elastomeric cross-linked polymer units and interconnected macropores containing living cells are produced by step of: in a mixture of the cells and elastomeric polymer units comprising activatable crosslinking groups, activating the crosslinking groups to form the scaffold.

20 Claims, No Drawings

MACROPOROUS 3-D SCAFFOLDS FOR TISSUE ENGINEERING

CROSS-REFERENCE TO RELATED APPLICATION

This application claims priority to U.S. Provisional Patent Application 61/672,038, filed Jul. 16, 2012, the entire contents of which are incorporated by reference.

INTRODUCTION

Methods for culturing cells in 3-dimensions (3D) have received growing attention in the field of tissue engineering, as the 3D approaches more closely mimic the microenvironment in which cells reside in vivo.[1-5] Extensive efforts have been dedicated towards developing 3D biomimetic scaffolds that incorporates biochemical, mechanical or architectural cues to facilitate desired cellular processes and tissue formation.[5-19] Hydrogels are a family of scaffolds widely used in tissue engineering applications due to its injectability, tissue-like water content, tunable biochemical properties, and ease for cell encapsulation.[5-11] However, most hydrogel-based scaffolds lack macroporosity (pore size larger than the size of cells), which may delay cell proliferation, migration, blood vessel ingrowth, or extracellular matrix (ECM) production.[20] Furthermore, hydrogel is often associated with weak mechanical strength, which limits their applications in engineering load-bearing tissues. Microfibers on the other hand, possess high mechanical strength and are frequently used as the building blocks to create highly porous scaffolds.[12-19] Microfibers can be bonded to form interconnected network that is inherently resilient to stress and deformation. Such network produces a large internal surface area that is amenable for modification to present biochemical cues. Microfiber-based scaffolds are typically macroporous, which provides ample 3D space that facilitates cell proliferation, migration and ECM production.

Various protocols have been developed to fabricate microfibers including macromolecule self-assembly,[12-13] micro-extrusion,[18-19] electrospinning,[14, 16-17] and template-assisted microfabrication.[15] Microfibers can then be bonded into a scaffold using solvent or chemical erosion,[15] solvent removal,[16-17, 19] or chemical crosslinking.[14, 18] However, these methods often involve the use of organic solvents, excess heat, high stress and harsh pH values, which are not cell-friendly. Therefore, cells can only be seeded onto microfiber scaffolds after the fabrication process, and left to grow into the microfiber scaffolds over time. Such processes often result in poor cell distribution and shallow cell penetration, which makes it difficult for applying microfibers to engineer tissues with clinically relevant dimensions.

Here we disclose crosslinkable hydrogels for fabricating macroporous and highly flexible tissue engineering scaffolds, and demonstrate their potential for supporting cell culture in 3D. The subject scaffolds combine the advantages from hydrogel and microfiber-based scaffolds, while overcoming the aforementioned limitations.

Non-woven fabrics (ex: U.S. Pat. No. 4,041,203, U.S. Pat. No. 5,188,885), electrospinning fibers (ex: U.S. Pat. No. 7,794,219), hydrogels for tissue engineering (ex: U.S. Pat. No. 7,854,923), wet-spinning method for making tissue engineering scaffolds (ex: U.S. Pat. No. 6,451,059).

Relevant art includes U.S. Pat. No. 8,017,107, U.S. Pat. No. 7,531,503, and U.S. Pat. No. 7,928,069.

SUMMARY OF THE INVENTION

The invention provides a method of making a macroporous 3-D tissue engineering scaffold comprising elastomeric cross-linked polymer units and interconnected macropores containing living cells, comprising the step of: in a mixture of the cells and elastomeric polymer units comprising activatable crosslinking groups, activating the crosslinking groups to form the scaffold.

The invention encompasses all combinations of particular embodiments:

the cells are homogeneously distributed though the scaffold;

the distribution of the cells within the scaffold is unachievable by cell migration from its surface;

the density of the cells does not decrease with distance from the surface;

the scaffold is at least 1, 4, 8, 16 cm$^3$;

the units comprise bioactive ligands that specifically interact with biomolecules of the cells or bind biomolecules that interact with biomolecules of the cells, to direct cell fate or induce the cells to form a tissue;

the bioactive ligands include: carboxyl, amine, phenol, guanidine, thiol, indole, imidazole, hydroxyl, sulfate, norbornene, maleimide, laminin, fibronectin, fibrinogen, peptide sequences, or combinations thereof;

the units have the shape of a sphere, an ellipsoid, a polyhedron, a cube, a rod, a sheet, a fiber, a ribbon, a helix, or a ring;

the polymer is a natural polymer, such as fibrin, fibrinogen, fibronectin, collagen, gelatin, dextran, chondroitin sulfate, alginate, chitosan, chitin, hyaluronic acid, heparin sulfate, a protein derivative, a nucleotide, a polysaccharide, and a glycosaminoglycan, or a synthetic polymer, such as poly (ethylene glycol), poly(lactic-co-glycolic acid), poly (glycolic acid), poly (lactic acid), polycaprolactone, poly(methyl methacrylate), polyurethane, and a silicone, or other polymer suitable for tissue engineering;

the scaffold has hydrogel-like viscoelasticity;

the macropores have cell-scale to one-order larger than cell-scale porosity, such as an average pore size is in the range 10-500 μm;

the scaffold has a density in the range 2.5 to 10% (wt/v);

the scaffold has a tunable compressive modulus from 0.3 kPa to 100 kPa the scaffold sustains 50, 60 70, 80, 90% strain and 20, 30, 35 MPa stress without failing;

the scaffold maintains more than 50% strain energy after being exposed to 60, 70% cyclic compression), the scaffold maintains more than 50% compressive modulus (at 20%, 30% strain) after receiving 70, 80% cyclic compressions;

the scaffold visually reverses to its original shape after receiving 60, 70, 80, 90% cyclic-strain;

as compression on the scaffold increases up to 90%, the density increases, and the compressive modulus of the scaffold increases non-linearly from about 20 kPa to 35,600 kPa the crosslinking groups are photo-, enzymatically-, chemically-, mechanically-, or heat-activatable;

the crosslinking groups are acrylic groups, methacrylic groups, vinyl groups, norbornene groups, maleimide groups, amine groups, thiol groups or polyelectrolytes;

the scaffold is saturated with a cell growth medium;

the activating initiates indirect crosslinking, via a binding compound (fibrinogen, fibronectin, laminin, polyelectrolyte, etc.) that binds to the crosslinking groups (acrylic, methacrylic, vinyl, norbornene, maleimide, amine, thiol groups);

the activating initiates direct crosslinking, via the crosslinking groups;

the scaffold is shaped as an implant e.g. for skin, fat, bone, skeletomuscular, cardiovascular, and cartilage tissues.

the scaffold is loaded with a drug and shaped as drug distribution vehicle;

the method comprises an additional or antecedent step of: converting a polymer precursor, which may be linear or branched into the polymer units, by for example, wet-spinning the precursor into microfibers; introducing the crosslinking groups onto the units; introducing bioactive ligands onto the units; and/or shaping the units into spheres, ellipsoids, polyhedrons, cubes, rods, sheets, fibers, ribbons, helices, or rings; and/or the method comprises the subsequent step of implanting the scaffold in a body.

The invention also provides a macroporous 3-D tissue engineering scaffold comprising elastomeric cross-linked polymer units and interconnected macropores containing living cells, as made by a disclosed method.

DESCRIPTION OF PARTICULAR EMBODIMENTS OF THE INVENTION

We have developed 3D scaffolds that distribute cells in a sizable 3D space, provide macroporosity to facilitate mass transport and cell growth, absorb stress and deformation, and incorporate biochemical cues to direct cell fate.

The invention provides a method of making a macroporous 3-D tissue engineering scaffold comprising elastomeric cross-linked polymer units and interconnected macropores containing living cells, comprising the step of: in a mixture of the cells and elastomeric polymer units comprising activatable crosslinking groups, activating the crosslinking groups to form the scaffold.

The crosslinking groups are activatable in that they form crosslinks when exposed to a crosslinking stimulus. Such crosslinks are typically covalent bonds. The crosslinks form in response to a biocompatible crosslinking stimulus. The crosslinking groups are photo-, electromagnetic-, enzymatically-, chemically-, mechanically-, or heat-activatable. Examples of suitable crosslinking groups are acrylic groups, methacrylic groups, vinyl groups, norbornene groups, maleimide groups, amine groups, thiol groups and polyelectrolytes, or combinations thereof.

The crosslinking groups may be located on the polymer units, or may be located on a binding compound (e.g., a small organic molecule that is added when forming the scaffold). A binding compound binds to a plurality (e.g., 2, 3, 4, 5, or more than 5) of polymer units. Examples of binding compounds are fibrinogen, fibronectin, laminin, and a polyelectrolyte.

The methods may include introducing or joining the crosslinking groups to the polymer units. Such introduction may involve reaction of groups already present on the polymer units, or may involve grafting new chemical groups onto the polymer units. The crosslinking groups may be protected groups that are de-protected via a suitable reagent or stimulus, e.g. protected carboxylic acid groups that are de-protected by exposure to an acid or another deprotecting agent.

A biocompatible crosslinking stimulus is one that initiates bond formation in the crosslinking groups but does not cause significant damage to the incorporated cells. Generally, biocompatible crosslinking stimuli involve mild pH values (e.g., between 6-8, or 6.5-7.5), mild temperatures (e.g., below 40, 35, 30, or 25° C.), and minimal or no organic solvents. Examples of biocompatible crosslinking stimuli include electromagnetic radiation (e.g., low-level UV or visible radiation), chemical (e.g., mild acids and bases), enzymatic, mechanical (e.g., agitation), and thermal stimuli (e.g., temperatures below 40° C.).

In some embodiments, the units comprise bioactive ligands. The bioactive ligands specifically interact with one or more biomolecules of cells or bind biomolecules that interact with biomolecules of the cells that are distributed within the scaffold or that proliferate within or migrate into the scaffold. Such interactions are effective to direct cell fate or induce the cells to form a tissue. The identity of the bioactive ligands will depend upon the identity of the target cells, and some examples of suitable bioactive ligands include: carboxyl, amine, phenol, guanidine, thiol, indole, imidazole, hydroxyl, sulfate, norbornene, maleimide, laminin, fibronectin, fibrinogen, peptide sequences, or combinations thereof.

By crosslinking the polymer units in the presence of the cells, the methods can provide cell distributions unachievable by methods which rely on cell invasion after crosslinking. For example, in particular embodiment the cells are substantially homogeneously distributed though the scaffold; the distribution of the cells within the scaffold is unachievable by cell migration from its surface; and/or the density of the cells does not significantly and substantially decrease with distance from the surface. In particular embodiments the cells are evenly distributed (variation less than 10 or 5%) across volumes of 0.1 or 1 $mm^3$ or along a transect or transects through the center of the scaffold.

A wide variety of cell types may be incorporated depending on the application, including mammalian cells (e.g. human), fungal cells, explanted primary or cultured cells, etc.

Crosslinking in the presence of the cells also permits the production of cell-containing scaffolds of essentially arbitrary sizes and shapes, without constraints otherwise imposed by the need to grow the cells into the scaffold. Hence, the methods may be used to produce small, e.g. subcutaneous, drug delivering scaffolds, or large tissue replacement, e.g. femur bone. In particular embodiments, the scaffold is at least 1, 4, 8, or 16 $cm^3$.

The units may comprise bioactive ligands that specifically interact with biomolecules of the cells or bind biomolecules that interact with biomolecules of the cells, to direct cell fate or induce the cells to form a tissue. A wide variety of bioactive ligands may be incorporated including carboxyl, amine, phenol, guanidine, thiol, indole, imidazole, hydroxyl, sulfate, norbornene, maleimide, laminin, fibronectin, fibrinogen, peptide sequences, or combinations thereof. The bioactive ligands may be introduced before or after formation of the polymer units (e.g. may involve grafting new chemical groups onto the polymer units) and may be protected groups that are de-protected via an appropriate reagent or stimulus.

The polymer units are non-crosslinked polymers (including oligomers) that are biocompatible with the cells. The polymer forming the polymer units may be natural or synthetic. Examples of natural polymers include polypeptides, polynucleotides, natural resins, rubbers, and polysaccharides. Examples of synthetic polymers include polystyrene, polypropylene, polyvinyl chloride, polyethers, polyesters, polyamides, polyimides, and organosilicon compounds.

The polymer units may have a shape that facilitates formation of the scaffolds. For example, the units may have the shape of a sphere, an ellipsoid, a polyhedron, a cube, a rod, a sheet, a fiber, a ribbon, a helix, or a ring.

The macropores have cell-scale to one-order larger than cell-scale porosity, based on the incorporated cell or cells. In particular embodiments, the average pore size is in the range of 10 to 100, 300 or 500 µm. In particular embodiments the average pore size is greater than 10, 20, 40, 80, 100 or 200 µm, and/or less than 500, 300, 200, 100, 80, 40 or 20 µm.

The scaffolds may be engineered to a wide varied of physical and mechanical properties. In particular embodiments the scaffold has hydrogel-like viscoelasticity, the scaffold has a density in the range 1, 1.5, 2 or 2.5 to 10, 15, 20 or 25%% (wt/v), the scaffold has a tunable compressive modulus from 0.3 kPa to 100 kPa, the scaffold sustains 50, 60 70, 80, 90% strain and 20, 30, 35 MPa stress without failing, the scaffold maintains more than 50% strain energy after being exposed to 60, 70% cyclic compression), the scaffold maintains more than 50% compressive modulus (at 20%, 30% strain) after receiving 70, 80% cyclic compressions, the scaffold visually reverses to its original shape after receiving 60, 70, 80, 90% cyclic-strain, and/or as compression on the scaffold increases up to 90%, the density increases, and the compressive modulus of the scaffold increases non-linearly from about 20 kPa to 35,600 kPa.

The method may comprise the antecedent step of converting a polymer precursor, which may be linear or branched, into the polymer units, such as by wet-spinning the precursor into microfibers or microtubes, electrospinning microfibers from the precursor, freeze-drying the precursor to form microfibers, emulsifying the precursor into microparticles, melting and ejecting the precursor through a mold to form microfibers or microtubes, hot or cold-drawing the precursor into microfibers or microtubes, nano or micro-imprinting the precursor into specific shapes, molding the precursor into specific shapes, or cutting a sheet of the precursor into stripes.

The methods may include forming the polymer units into any of these (or another) shapes. In some embodiments, the polymer units are microribbons having an aspect ratio of less than 1, 0.5, 0.3, or 0.1, or having an aspect ratio of greater than 5, 6, 7, 8, 9, or 10. Such microribbons may have an average length that is 10, 50, 100, 200, or 500 times greater than their average width.

In some embodiments, the scaffolds are saturated with medium that facilitates cell growth or survival, i.e. a cell growth medium. In some embodiments, the scaffold may be impregnated with a drug or other material intended for delivery to a patient. For example, the scaffold may be intended for application on, or implantation in, the patient, and may be loaded with a drug to be delivered to the application or implantation site. Accordingly, the methods may involve applying the scaffold or implanting the scaffold onto/into a site on/in the body of a patient.

The scaffolds are suitable for a variety of applications, including regenerative medicine and tissue engineering. The inventive polymer units and scaffolds are suitable for: a 2D/3D scaffold for in vitro cell culture/study, including cell-based drug screening in a 3D format; a 3D platform for cell culture and expansion; a 2D/3D scaffold for in vitro cell culture and subsequently in vivo implantation, such as implants for skin, fat, bone, skeletomuscular, cardiovascular, and cartilage tissues; an acellular implantation for body tissues, such as skin, fat, bone, muscle, skeletomuscular, cardiovascular, or cartilage tissue; a drug distribution vehicle; and a framework that mechanically supports a tissue engineering construct.

The scaffolds are particularly useful as tissue engineering scaffolds. Thus, they may be used to facilitate cell proliferation and tissue formation. The macroporosity is suitable to allow cellular migration, formation of intracellular matrix, supply of nutrients, angiogenesis, and the like. The scaffold material is biocompatible and, in some embodiments, biodegradable or physiologically absorbable such that the scaffold may be implanted into a body and allowed to biodegrade after a suitable period of time.

The scaffolds are a suitable biomaterial to directly encapsulate cells and to culture the cells in 3D. The scaffolds are capable of achieving homogeneously distributed cells in a sizable 3D space, macroporosity for facilitating mass transport and cell growth, physical properties suitable for absorbing stress and deformation, and incorporated biochemical cues to direct cell fate. The scaffolds have highly interconnected macropores that promote nutrient diffusion and facilitate cell growth, spreading, migration and cell-cell communication and cell migration. The scaffolds exhibit large internal surface area that provides a large capacity for the proliferation of cells. The scaffolds can be customized with a broad range of stiffness, covering a range that is most relevant to tissue engineering application, such as 0 to 100 kPa. The scaffolds can sustain a large loading and deformation, and are a suitable biomaterial to regenerate load-bearing tissues, like cartilage and bones.

DESCRIPTION OF ALTERNATIVE EMBODIMENTS

We disclose 3D tissue engineering scaffolds with interconnected macropores made by crosslinking a set of polymer building blocks of certain shapes. Our invention satisfies fundamental requirements of tissue engineering, including: (1) distribute cells in 3D, (2) facilitate nutrient transport, (3) support cell migration and growth, (4) facilitate cell production of tissues, and (5) sustain loading and deformation.

In one aspect our invention provides an inter-crosslinkable polymer unit for culturing cells, and making a tissue engineering scaffold. Such polymer units can be crosslinked together utilizing a bonding compound, which bonds together the polymer units, forming a network that forms interconnected pores. Such network absorbs stress and deformation by distributing an exterior force throughout the network of polymer units. The polymer unit has a shape that facilitates the absorption of stress and the formation of pores in the scaffold. The polymer unit can incorporate a set of biochemical ligands to interact with living cells, inducing the bioactivities for tissues formation.

In another aspect, our invention is a method to fabricate a porous tissue engineering scaffold. The scaffold supports cell viability and also the bioactivities for tissue formation, such as cell migration and production of ECM. The method may include the steps of: Prepare a polymer precursor; convert the polymer precursor into polymer units that contains a set of crosslinking groups; and inter-crosslink the polymer units via the crosslinking groups, forming the scaffold, which can be carried out in the presence of living cells.

In another aspect, our invention is a fabrication platform to produce polymer units that serve as the building blocks for making tissue engineering scaffolds, e.g. A platform to fabricate polymer units that can be inter-crosslinked to form a tissue engineering scaffold. Such polymer unit has a shape that facilitates the formation of interconnected pores in the scaffold. Our platform can include the following parts: (a) a first device that shapes a precursor material into the shape by causing a force onto the precursor material, and stabilizes the shape by causing a change to the precursor material; (b) a second device that modifies the precursor material with a crosslinking group, which enables the polymer units to be bonded together; and (c) a feeding device that supplies the precursor material to the first device.

The shape of the polymer unit can be an irregular geometry. The shape of the polymer can be a regular geometry, such as a sphere, an ellipsoid, a polyhedron, a cube, a rod, a sheet, a fiber, a ribbon, a helix, or a ring. The first device can include a tank of primary solvent and a rotating vane, wherein the shape is a fiber and the force is the shear-stress generated in the primary solvent by the rotating vane. The first device can include at least one inlet and a spindle, wherein the shape is a fiber, the inlet introduces the precursor material, the spindle rotates to stretch the precursor material from the inlet, and the force is the tension between the spindle and the inlet. The first device can include a primary solvent with a surfactant, wherein the shape is a sphere, the force is the surface tension tuned by the surfactant. The first device can include a rotating container that has at least one hole, wherein the shape is a fiber, the force is the centrifuge force from the rotation of the container, and such centrifuge force ejects the precursor material from the hole. The first container can include an inlet, a collector, and a power generator that causes a voltage between the inlet and the collector, wherein, the shape is a fiber, the force is the electrostatic force caused by the voltage, and such electrostatic force draws the precursor material from the inlet to the collector. The first device can include a primary solvent in which the precursor material is insoluble, wherein the change is a precipitation of the precursor material in the primary solvent. The first device can introduce a cross-linker molecule, wherein the precursor material can be one that crosslinks in the presence of the cross-linker molecule, and the change is the crosslinking of the precursor material. The first device can include a cutter to cut the precursor material into the shape. The change can be a phase change from a liquid to a solid. The change can be a phase change from a liquid to a gel. The precursor material can be a polymer dissolved in a secondary solvent. The precursor material can be a polymer at liquid phase. The second device can modify the precursor material after the first device fixes the shape of the precursor material. The second device can modify the precursor material before the first device shapes the precursor material. The second device can modify the precursor material before the first device fixes the precursor material.

We have created a new type of material for making tissue engineering scaffold, the "microribbons". The microribbon is a long and flat elastomer that maintains the linear shape of microfibers and at the same time possesses the viscoelasticity of hydrogels. Most remarkably, the microribbons can be crosslinked together in the presence of cells. The crosslinking procedure takes place under a biocompatible condition with the stimulation of light and turns the microribbons into a 3D scaffold with good stiffness and highly-interconnected macroporosity. In one example our microribbons are made from gelatin, which is a naturally occurring, cost-efficient biopolymer that has been used extensively for cell culture and tissue engineering applications. Gelatin is derived from collagen and thus contains an abundance of cell-adhesion sequences on its protein chains. Such biochemical property enables cells to spread on the microribbons and migrate within the 3D network formed by the microribbons. In addition we have also used our methods to synthesize other kinds of polymer units, and crosslinked them to form macroporous scaffolds, including gelatin microspheres and poly (ethylene glycol) microfibers, both of which provide macroporosity to allow cell growth and migration.

Our invention is designed for the application of regenerative medicine and tissue engineering in general, and the polymer units and the scaffold can be specifically used for: (a) a 2D/3D scaffold for in vitro cell culture/study, including cell-based drug screening in a 3D format; (b) a 3D platform for cell culture and expansion; (c) a 2D/3D scaffold for in vitro cell culture and subsequently in vivo implantation, such as implants for skin, fat, bone, skeletomuscular, cardiovascular, and cartilage tissues; (d) an acellular implantation for body tissues, such as skin, fat, bone, muscle, skeletomuscular, cardiovascular, or cartilage tissues; (e) a drug distribution vehicle; (f) a framework that mechanically supports a tissue engineering construct.

Our cell studies and mechanical testing have shown that these structures are an outstanding biomaterial to directly encapsulate cells and to culture the cells in 3D. Such results evidence that the scaffold of our invention has satisfied all the important functions for a tissue engineering scaffold, including (1) Distribute cells in a sizable 3D space, (2) provide macroporosity to facilitate mass transport and cell growth, (3) absorb stress and deformation, and (4) incorporate biochemical cues to direct cell fate.

More specifically, the scaffolds have the following advantages: (a) direct cell encapsulation allows a good control of cell distribution in 3D; (d) highly interconnected macropores promote nutrient diffusion and facilitate cell growth, spreading, migration and cell-cell communication also cell migration; (3) large internal surface area produce a large capacity for the proliferation of cells; (4) scaffolds can be customized with a broad range of stiffness, covering a range that is most relevant to tissue engineering application—0 to 100 kPa; (5) Since the scaffolds can sustain a large loading and deformation, they are a perspective biomaterial to regenerate load-bearing tissues, namely, cartilage and bones.

In contrast to the disadvantage of conventional hydrogel scaffolds, which contain no interconnected macroporosity and thus limit the extent of proliferation/migration of cells, the scaffold of our invention is a biopolymer network with highly interconnected macroporosity. Such network facilitates the important bioactivities for tissue formation, including cell proliferation, migration, and producing of ECM components.

In contrast to the disadvantage of conventional macroporous scaffolds, which are unable to directly encapsulate cells in 3D, the polymer units of our invention are able to form a macroporous 3D network in the presence of cells, such feature facilitates a good control of cell distribution in a sizable 3D scaffold.

Fundamentally our invention creates a porous tissue engineering scaffold by intercrosslinking a set of polymer building blocks (units) of certain geometries (shapes).

The invention provides a platform for 3D cell culture/expansion. Conventional cell expansion is carried out on a 2D surface, such as on a Petri dish. When such 2D surface is saturated by the proliferated cells (confluency), cell expansion has to be halted, with cells released by enzyme and distributed onto more culture dishes (passaged). Such change not only creates a shock that potentially affects the stability of cell phenotypes but also requires significant amount of time and labor. As the researches of cell/stem-cell based therapies are gradually developed toward large-throughput studies and clinical applications, the conventional 2D setting is causing a bottom-line cost and limitation to the companies that profit by providing cells for the research and medical institutes. In contrast to the conventional 2D setting, the scaffold of our invention contains a large internal surface area on which cells can grow, and thus can serve as a significantly more efficient culturing platform for cell expansion. For example, the proliferation rate of hADSCs from a standard 2D cell culture is normally 4-6 fold per flask/dish per passage; however, the result from our embodiment shows that the proliferation rate of hADSCs reaches more than 30 fold in 3 weeks in our 3D scaffold with ribbon-like polymer units, with such growth continued. This result demonstrates that culturing cells in our 3D setting is highly efficient and may replace the conventional 2D settings for producing a large number of cells from a single batch. For this kind of application, we can use conventional polystyrene to form the polymer units for the macroporous scaffold.

The invention provides a scaffold for plastic surgery. Plastic surgeries often use 3D implants that are centimeter-thick to compensate defects. As cell-based therapies are adopted it is important to provide physicians a choice to use a 3D biomaterial that facilitates cell bioactivities which lead to host-tissue formation, such as cell migration, proliferation, and producing ECM components including collagens and glycoaminoglycans. As demonstrated by our experimental results, the current invention can effectively support such tissue formation. Moreover, the polymer building blocks of our invention can be inter-crosslinked into any shape of scaffold, allowing physicians to tailor the implant based on the dimensions of the defects.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

I. Microribbon-Like Elastomers for Fabricating Macroporous and Highly Flexible Scaffolds that Support Cell Proliferation in 3D In this example we demonstrate microribbons made from gelatin, which contains abundant ECM cues and widely used for tissue engineering applications.[11, 21-23] We examined the effects of fabrication parameters on microribbon properties by varying ejection rate, drying temperature, time of pre-fixation and drying agent, and characterized the resulting scaffold morphology using scanning electron microscopy. The ability of microribbon-based scaffolds to support cell culture was evaluated by quantifying cell spreading, attachment, and proliferation over time. Mechanical property of microribbon-based scaffold was examined using compression test and compared to scaffolds fabricated from microfiber counterparts.

Synthesizing Gelatin Microribbons by Wet-Spinning

Our procedure to fabricate the microribbons started with a wet-spinning process of gelatin. We chose gelatin, a digested form of collagen, due to its high biomimetic nature and abundance of cell-adhesion sites, which would facilitate cell spreading and migration within the 3D microribbon network. Type-A gelatin (GelA) dissolved in dimethyl sulfoxide (DMSO) was injected from a syringe pump into a bath of anhydrous ethanol with constant stirring. Pulled by gravity and stabilized by a high surface tension, the ejected GelA solution dripped unbrokenly and formed a fine thread, which flowed continuously into the ethanol bath. Since ethanol is a miscible agent to DMSO but an anti-solvent to gelatin, the GelA thread rapidly dried upon contact with ethanol bath and turned into a cluster of microfibers. Constant stirring of ethanol caused a shear flow that further narrowed the GelA thread and spun the resulting microfibers into cotton-like bundles.

After the wet-spinning, the microfibers were transferred and dried in acetone bath for 3 hours at either 25° C. or 60° C. Under both temperatures, drying by acetone caused a rapid and asymmetrical collapse of microfibers, which led to the formation of microribbon structure. The as-formed microribbons were washed 3-times by ethanol and then dissociated into short segments (<1 mm in length) using a homogenizer. The microribbons were then treated with methacrylic anhydride, which methacrylated lysines in the microribbons to introduce methacrylate groups onto the microribbon to allow photocrosslinking. To pre-crosslink the microribbons and make them water-insoluble, the methacrylated microribbons were further treated with glutaraldehyde at 40° C. for either 3 or 12 hours. The aldehyde-fixed microribbons were finally neutralized by a lysine solution. Upon exposure to light, the gelatin microribbons crosslinked like hydrogels and formed a macroporous gelatin network. The resulting scaffold demonstrated a sponge-like physical property and maintained integrity upon squeezing.

Effects of Fabrication Parameters on Microribbon Properties

The physical and chemical properties of microribbons can be tuned by varying the parameters from fabrication process. The parameters we investigated included the rate of ejection (5 or 10 mL/hr), the temperature for post-spinning drying (25 or 60° C.), the time for glutaraldehyde fixation (3 or 12 hrs), and the choice of drying agent (acetone or methanol).

Morphology of the Microribbons-Based Scaffolds

To explore the effects of varying microribbon concentration on the morphology of resulting scaffolds, microribbons with increasing densities (2.5, 5, 7.5, and 10% wt/v) were photocrosslinked and characterized using scanning electron microscopy (SEM) imaging. Upon exposure to light, gelatin microribbons fused into a macroporous scaffold resembling a "highway system" that facilitates cell migration and interactions throughout the whole scaffold. The space among microribbons formed interconnected macroporous channels, which offer ample space for nutrients diffusion, cell proliferation, and matrix production. While increasing microribbon density provides more internal surface area to support cell proliferation, it also reduces the macroporosity of scaffold. The diameter of the interconnected pores is inversely related to the density of microribbons, and increasing the density of microribbons from 2.5 to 10% (wt/v) led to a decrease in pore size from about 200 µm to 50 µm. Scaffolds with higher microribbon density also demonstrated more fusion between neighboring microribbons, which further reduced the pore size. Increasing the feeding rate of GelA solution during wet spinning led to wider microribbons. The microribbons produced at 5 mL/hr were 20-50 µm wide, and the ones produced at 10 mL/hr were 60-90 µm wide.

Cell Spreading and Alignment on Microribbons

To examine whether microribbons support cell culture, human adipose-derived stromal cells (hADSCs) (passage 3) were cultured on dissociated microribbons. Cell morphology and spreading was monitored over time by fluorescence imaging. Two types of microribbons were examined: R10-T25-G12-A and R10-T60-G12-A—the former was dried in acetone at 25° C. and the later at 60° C. Given that proteins tend to unfold secondary and tertiary structures at elevated temperatures,[24-25] we hypothesize that heating at 60° C. would induce changes in the biophysical and biochemical properties of gelatin microribbons, which may lead to different cellular behavior. Fluorescence imaging showed both types of microribbons supported the spreading and growth of hADSCs. Cells started to attach and spread on the microribbons 3 hours after cell seeding, and continued to spread and proliferate up to day 16. These results demonstrate that our gelatin microribbons not only facilitate cell encapsulation, but also support cell spreading and proliferation. Furthermore, both types of microribbons (dried at 25° C. or 60° C.) promoted cell alignment along the direction of the microribbons. Elevating drying temperature from 25° C. to 60° C. led to enhanced cell spreading and alignment. Heating can be used to help unfold gelatin molecule and expose more cell-binding sites on the surface of microribbons.

Cell Proliferation in Photocrosslinked Microribbon Scaffolds in 3D

To evaluate the scaffolds for culturing cells in 3D, hADSCs were encapsulated in photocrosslinked microribbon scaffolds. Cells were mixed with microribbons, and upon exposure to light the microribbons crosslinked into a 3D scaffold with cells distributed throughout the scaffold. Fluorescence imaging demonstrated that microribbon scaffolds are highly supportive for cell proliferation. Cell number increased dramatically over time and reached confluence by day 13.

To further quantify the effects of drying condition on cell proliferation in 3D, two types of microribbons, dried at 25° C. or 60° C. respectively, were used to culture hADSCs. Cell number was quantified using MTS assay over time up to 20 days. For each type of microribbon, four groups of scaffolds were fabricated by varying concentration of the microribbons: 2.5, 5, 7.5, and 10% (w/w). Although all groups started with the same cell number at the time of encapsulation (5 million cells/mL), difference in cell number can be detected as early as day 1, with the lowest cell number detected in the groups fabricated with 2.5% (wt/v) of microribbons. Scaffolds fabricated using the lowest percentage of microribbon also correlate with highest porosity, which may lead to low seeding efficiency due to cells falling out through the pores before they adhere to the microribbons. Dramatic cell proliferation was observed over time in all groups, and cell number increased up to 30 folds from day 1 to 20.

Cell proliferation in scaffolds with varying microribbon density was comparable overall, with no statistical significance among each other. The cell number in the groups of 2.5 wt % microribbons reached plateau earlier, probably due to the more porosity available for cells to proliferate. Cell proliferation in scaffolds of higher microribbon density (7.5 and 10% wt/v) demonstrated a continuous increase over time up to day 20. As the microribbon density increases, the resulting scaffolds provide larger internal surface area for cell attachment and proliferation. Meanwhile, increasing microribbon density also decreased the macroporosity, which may also limit cell proliferation. Such counter-balance effects on cell proliferation may explain the comparable total cell number across groups with different microribbon density. Furthermore, cell proliferation increased by 5-20% in microribbons dried at 60° C. compared to their respective controls that were dried at 25° C. This is consistent with our earlier observation that heated-microribbons promote cell spreading.

Altogether, our results show that microribbons-based scaffolds enable encapsulating cells in 3D and support cell adhesion, spreading and cell proliferation in 3D. The photocrosslinkable microribbon-based scaffolds reported herein combine the strength of traditional hydrogel or microfiber scaffolds while avoiding the associated limitations. The gelatin-based microribbons are highly biomimetic, and its hydrogel-like water content provides a suitable microenvironment for cell culture. Unlike traditional hydrogels, which are often nanoporous, the photocrosslinked microribbon scaffolds possess large internal surface area and highly interconnected macropores, which promote cell adhesion, proliferation and matrix production. Furthermore, since the microribbons promote cell alignment, they hold great promise as scaffolds for regenerating tissues with anisotropic nature, such as nerves, muscles, and cardiovascular tissues, in which cell alignment are highly desirable for tissue functions.

Mechanical Property of Microribbon-Based Scaffolds

Mechanical property is an important aspect of tissue engineering scaffolds, and determines whether the scaffolds can be used for engineering load-bearing tissues such as bone or cartilage. Furthermore, stiffness of the scaffolds themselves provides biophysical cues to directly influence cell fates.[26-27] Compressive modulus measurement was performed to characterize the mechanical property of microribbon-based scaffolds fabricated using varying microribbon width, density, and drying temperature. Increasing the density of microribbons led to a non-linear increase in the stiffness of scaffolds, with a large range of tunable compressive modulus from 0.3 kPa to ~100 kPa. A small increase in microribbon stiffness was observed when density increased from 2.5% to 5% (w/w), and the overall compressive modulus remained low (~6 kPa). Further increases in microribbon density to 10% led to over 10-30 fold increase in compressive modulus of the resulting scaffolds compared to their 5% controls. This is likely due to the fact that microribbons fuse with each other to form a stronger network when the density was increased from 5% to 10% (w/w). Increasing microribbon width from 40 µm to 70 µm led to a 100% increase in scaffold compressive modulus at high concentration range (10%) (p=0.013). Increasing drying temperature to 60° C. led to a slight increase in scaffold modulus at high microribbon concentration (10% w/w), while not much difference was observed at lower microribbon concentration groups.

Effects of Glutaraldehyde Fixation on Scaffold Morphology and Mechanical Property Gelatin is a protein based material and can be crosslinked using glutaraldehyde prior to photocrosslinking. By varying the degree of glutaraldehyde treatment, we can further tune the morphology and mechanical property of the resulting scaffolds. Short glutaraldehyde treatment (3 hrs) led to partially crosslinked microribbons, which were soluble in water at 37° C. Increasing glutaraldehyde treatment up to 12 hrs led to much more stable microribbons, which remain physically stable in water at 37° C. for more than a week. Upon photocrosslinking, 12-hr-fixed microribbons maintained their shape while 3-hr-fixed microribbons fused with each other with decreased pore size. The less-fixed microribbons have higher mobility that allows the methacrylate groups to form stronger inter-crosslinked networks, which led to 3-5 fold increase in mechanical strength of the resulting scaffolds.

Enhanced Flexibility of Microribbon-Based Scaffolds Vs. Microfiber-Based Scaffolds Unlike the conventional microfibers, the novel microribbons reported here is characterized by the high aspect ratio of cross section, which resembles strip-springs. We hypothesize that such unique microstructures would convey enhanced flexibility and resilience when challenged by mechanical stress. To test our hypothesis, we fabricated two types of scaffolds using either microribbons or microfibers as the building blocks. All the parameters were kept the same except the drying agent, which led to different aspect ratio of cross section. Drying the gelatin fibers in acetone led to a rapid asymmetric collapse and formation of microribbons with flat cross sections. In contrast, replacing acetone by methanol led to a symmetrical drying, which produced microfibers with round cross sections. The microfibers shared the same biochemical and surface properties as the microribbons, and formed macroporous scaffolds upon photocrosslinking. Our compressive testing showed dramatically enhanced flexibility in microribbon-based scaffolds compared to the microfiber-based scaffolds. Microribbon-based scaffolds (5% w/w) can be compressed up to 90% strain and instantly reversed to its original shape upon the removal of external force. In contrast, microfiber-based scaffolds (5% w/w) underwent permanent deformation when the compressive strain exceeded 60%.

To quantify the flexibility and resilience of microribbon- and microfiber-based scaffolds, we applied cyclic compressions (10 times for each strain) to scaffolds and analyzed the resulting stress responses using stress-strain data. Up to 70% strain level, the microribbon-based scaffolds performed consistent (less than 10% change) stress responses for 10 compression cycles, indicating insignificant damage during the cyclic compressions. In contrast, when the strain level exceeded 40%, the microfiber-based scaffolds showed inconsistent stress responses during the 10 compression cycles, suggesting that substantial damage had taken place.

The damage from cyclic-compression was further measured by the changes in strain energy, compressive modulus, and scaffold appearance. The microribbon-based scaffolds maintained more than 50% strain energy after being exposed to 70% cyclic compressions, while the microfiber-based scaffolds lost more than 50% strain energy after being exposed to 60% cyclic compressions. Furthermore, the microribbon-based scaffold maintained more than 50% compressive modulus (at 20%~30% strain) after receiving 80% cyclic compressions, while the microfiber-based scaffolds lost more than 50% modulus after receiving 70% cyclic compressions. Visually, the microribbon-based scaffolds reversed to their original shapes after receiving 90% cyclic-strain, while the microfiber-based scaffolds gradually fell apart as the cyclic-strain level exceeded 60%.

Such exceptional flexibility and resilience of the microribbon-based scaffolds has not been previously reported on any other microfiber-based scaffolds, most of which comprise symmetric cross-section microfibers and lack the similar capacity to absorb stress and deformation. The flexibility of microribbon-based scaffold also significantly surpasses that of typical hydrogel scaffolds, which often undergo mechanical failure at a much lower strain rate (<50%).[28]

As the compression on microribbon-based scaffold increased up to 90%, the microribbon density increased drastically, and the compressive modulus of the microribbon scaffold increased non-linearly from about 20 kPa to 35,600 kPa (or 35.6 MPa). This strain-induced hardening and the range of modulus change covers the stiffness range of many tissue types including nerve (~30 kPa), skin (0.4~0.9 MPa), artery (0.1~1 MPa) and articular cartilage (1~20 MPa).[29-32] Thus the microribbons are suitable for engineering a broad range of tissue types, from the soft and highly elastic tissues to load-bearing hard tissues. Since flexibility and shock-absorption are crucial functions for cartilage, these highly flexible microribbon-based scaffolds are particularly useful in engineering cartilage tissues, such as intervertebral disc, meniscus, and articular cartilage.[33-36]

Mechanical Testing:

Unconfined compression tests were conducted using an Instron 5944 materials testing system (Instron Corporation, Norwood, Mass.) fitted with a 10 N load cell (Interface Inc., Scottsdale, Az). The test set-up consisted of custom made aluminum compression platens lined with PTFE to minimize friction. All tests were conducted in PBS solution at room temperature. Before each test, the scaffold's diameter (~4.5 mm) and thickness (~2.5 mm) were measured using digital calipers A preload of approximately 2 mN was applied to ensure the scaffold surface was in full contact with the upper platen. To measure compressive modulus, the upper platen was lowered at a rate of 1% strain/sec to a maximum strain of 15%. Load and displacement data were recorded at 100 Hz. Stress vs. strain curves were created and curve fit using a third order polynomial equation. The compressive modulus of scaffold was determined from the curve fit equation at strain values of 5%, 10%, and 15%.

Flexibility Evaluation:

To evaluate scaffold flexibility, cyclic compressions were applied to the microribbon-based and microfiber-based scaffolds (5 wt %) at strain levels of 30, 40, 50, 60, 70, 80, and 90 percents. For each strain level, scaffolds (n=5) were compressed and released for ten cycles at the rate of 5%/sec. The loading and displacement data was recorded at 10 Hz, and for each compression cycle the strain energy density (in $J/m^3$) at 30% strain was calculated numerically using the following equation ($Es_{30\%}$: strain energy density at 30% strain, $$P: \text{stress}, \epsilon: \text{strain}): Es_{30\%} = \int_0^{0.3} P(\epsilon) d\epsilon \qquad (1)$$

The change (decrease) at $Es_{30\%}$ was associated with the damage at scaffold networks upon cyclic compressions, and thus $Es_{30\%}$ was used as the indicator of scaffold flexibility: the scaffolds with less-decreased $Es_{30\%}$ upon cyclic loading were considered more flexible and resilient. In addition to quantitative measurements, scaffold flexibility was also evaluated visually based on the scaffolds' structure integrity upon cyclic compressions.

In conclusion, here we report the development of a novel, microribbon-based scaffold with exceptional mechanical flexibility that facilitates cell growth and tissue formation in 3D. Each microribbon is a long and flat elastomer that possesses the viscoelasticity of hydrogels. The interconnected macroporosity of the microribbons support cells adhesion, spreading and alignment, leading to cell proliferation by up to 30 fold within 3 weeks. Cellular responses and mechanical properties of the microribbon-based scaffold can be tuned easily by varying fabrication parameters including the wet-spinning rate, drying temperature, choice of drying agent, level of pre-fixation, and the density of microribbons. The scaffold formed by the microribbons can sustain up to 90% strain and 3 MPa stress without failing, and such exceptional flexibility and resilience would provide a particularly useful scaffold for engineering shock-absorbing tissues such as cartilage and spines.

REFERENCES

[1] E. Cukierman, R. Pankov, D. R. Stevens, K. M. Yamada, *Science* 2001, 294, 1708.
[2] T. Jacks, R. A. Weinberg, *Cell* 2002, 111, 923.
[3] A. Abbott, *Nature* 2003, 424, 870.
[4] J. Debnath, K. R. Mills, N. L. Collins, M. J. Reginato, S. K. Muthuswamy, J. S. Brugge, *Cell* 2002, 111, 29.
[5] K. A. Mosiewicz, K. Johnsson, M. P. Lutolf, *J. Am. Chem. Soc.* 2010, 132, 5972.
[6] C. A. DeForest, B. D. Polizzotti, K. S. Anseth, *Nat. Mater.* 2009, 8, 659.
[7] C. J. Flaim, S. Chien, S, N. Bhatia, *Nat. Methods*. 2005, 2, 119.
[8] Y. Soen, A. Mori, T. D. Palmer, P. O. Brown, *Mol. Syst. Biol.* 2006, 2, 37.
[9] J. A. Benton, B. D. Fairbanks, K. S. Anseth, *Biomaterials* 2009, 30, 6593.
[10] O. Jeon, K. H. Bouhadir, J. M. Mansour, E. Alsberg, *Biomaterials* 2009, 30, 2724.
[11] J. W. Nichol, S. T. Koshy, H. Bae, C. M. Hwang, S. Yamanlar, A. Khademhosseini, *Biomaterials* 2010, 31, 5536.
[12] J. D. Hartgerink, E. Beniash, S. I. Stupp, *Science* 2001, 294, 1684.

[13] M. Ma, Y. Kuang, Y. Gao, Y. Zhang, P. Gao, B. Xu, *J. Am. Chem. Soc.* 2010, 132, 2719.

[14] J. Rnjak, Z. Li, P. K. Maitz, S. G. Wise, A. S. Weiss, *Biomaterials* 2009, 30, 6469.

[15] C. P. Fik, M. Meuris, U. Salz, T. Bock, J. C. Tiller, *Adv. Mater.* 2011, 23, 3565

[16] R. J. DeVolder, H. Bae, J. Lee, H. Kong, *Adv. Mater.* 2011, 23, 3139.

[17] S. Y. Chew, R. Mi, A. Hoke, K. W. Leong, *Adv. Funct. Mater.* 2007, 17, 1288.

[18] R. A. Barry, R. F. Shepherd, J. N. Hanson, R. G. Nuzzo, P. Wiltzius, J. A. Lewis, *Adv. Mater.* 2009, 21, 2407.

[19] K. D. Nelson, A. Romero, P. Waggoner, B. Crow, A. Borneman, G. M. Smith, *Tissue Eng.* 2003, 9, 1323.

[20] S. J. Hollister, *Nat. Mater.* 2005, 4, 518.

[21] A. I. Van Den Bulcke, B. Bogdanov, N. De Rooze, E. H. Schacht, M. Cornelissen, H. Berghmans, *Biomacromolecules* 2000, 1, 31.

[22] H. Wang, M. B. Hansen, D. W. Lowik, J. C. van Hest, Y. Li, J. A. Jansen, S. C. Leeuwenburgh, *Adv. Mater.* 2011, 23, H119.

[23] A. Ovsianikov, A. Deiwick, S. Van Vlierberghe, P. Dubruel, L. Moller, G. Drager, B. Chichkov, *Biomacromolecules* 2011, 12, 851.

[24] J. L. Gornall, E. M. Terentjev, *Phys. Rev. Lett.* 2007, 99, 028304.

[25] D. Eagland, G. Pilling, R. G. Wheeler, *Faraday Discuss. Chem. Soc.* 1974, 181.

[26] D. E. Discher, P. Janmey, Y. L. Wang, *Science* 2005, 310, 1139.

[27] A. J. Engler, S. Sen, H. L. Sweeney, D. E. Discher, *Cell* 2006, 126, 677.

[28] J. A. Burdick, C. Chung, X. Jia, M. A. Randolph, R. Langer, *Biomacromolecules* 2005, 6, 386.

[29] K. Hirakawa, K. Hashizume, T. Hayashi, *No To Shinkei* 1981, 33, 1057.

[30] P. G. Agache, C. Monneur, J. L. Leveque, J. De Rigal, *Arch. Dermatol. Res.* 1980, 269, 221.

[31] H. Hasegawa, H. Kanai, Y. Koiwa, *IEEE Trans. Ultrason. Ferroelectr. Freq. Control* 2004, 51, 93.

[32] G. Bellucci, B. B. Seedhom, *Rheumatology (Oxford)* 2001, 40, 1337.

[33] Y. Shikinami, Y. Kotani, B. W. Cunningham, K. Abumi, K. Kaneda, *Adv. Funct. Mater.* 2004, 14, 1039.

[34] C. J. Spaans, V. W. Belgraver, O. Rienstra, J. H. de Groot, R. P. Veth, A. J. Pennings, *Biomaterials* 2000, 21, 2453.

[35] B. M. Baker, R. P. Shah, A. H. Huang, R. L. Mauck, *Tissue. Eng. A* 2011, 17, 1445.

[36] N. L. Nerurkar, B. M. Baker, S. Sen, E. E. Wible, D. M. Elliott, R. L. Mauck, *Nat. Mater.* 2009, 8, 986.

[37] P. A. Zuk, M. Zhu, H. Mizuno, J. Huang, J. W. Futrell, A. J. Katz, P. Benhaim, H. P. Lorenz, M. H. Hedrick, *Tissue Eng.* 2001, 7, 211.

II. Photocrosslinkable PEG-Based Microribbons for Forming 3D Macroporous Scaffolds with Decoupled Niche Properties The extracellular matrix (ECM) is a three-dimensional (3D) multi-factorial microenvironment, and cell fate is dictated by complex, interactive niche signals including biochemical, mechanical, and topographical cues[1-3]. To promote desirable cellular processes and tissue formation, extensive attempts have been made to develop biomaterials as artificial niche that mimics the biochemical and mechanical properties of ECM[4-10]. Recent studies have shown that scaffold topographical cues, such as macroporosity and surface curvature, can also be engineered to promote cell proliferation, vascularization, and tissue formation[11-16]. Given cell-ECM often interact in a complex and non-intuitive manner, macroporous scaffolds that possess decoupled niche properties would be highly desirable to facilitate elucidating how interactive niche signals regulate cell fates and tissue formation. Towards this goal, here we report the development of 3D scaffolds with decoupled biochemical, mechanical and topographical properties using microribbon-like, poly (ethylene glycol) (PEG)-based hydrogels, which can further intercrosslink to form 3D macroporous scaffolds that allow the direct encapsulation of cells.

A few recent studies have attempted to create hydrogel-based scaffolds with decoupled biochemical and mechanical properties[5-8], however, these platforms generally have limited tunability of topographical properties. Furthermore, current methods to introduce topographical cues into 3D scaffolds often involve non-physiological fabrication conditions, such as stereolithography, electrospinning, lyophilizing and salt-leaching[17-20]. As a result, cells can only be seeded post scaffold fabrication, which often results in nonuniform cell distribution and tissue formation[19, 21-23]. Recently, we reported the development of a cell-friendly process for fabricating macroporous scaffolds using gelatin-based, microribbon-like hydrogels as building blocks, which can further crosslink together to form 3D scaffolds with tunable macroporosity[13]. The resulting scaffold supported rapid cell proliferation of human adipose-derived stromal cells in 3D, and demonstrate great mechanical flexibility when subject to cyclic compression. One limitation that remains with the gelatin-based microribbon scaffold is that as a collagen-derived natural biomaterial, it is subject to potential batch-to-batch variability, and does not allow decoupled tunability of biochemical and mechanical cues.

As such, the goal of this study is to develop synthetic polymer-based microribbons as building blocks for forming 3D macroporous scaffolds with independently tunable biochemical, mechanical and topographical cues that support direct cell-encapsulation. We have chosen 8-arm PEG with different functional end-groups as the base materials given its biological inertness and amenability to chemical modification[24]. We first produced PEG hydrogels with microribbon-like structures by wet-spinning 8-arm PEG structures with different end-group chemistry. The stiffness of the wet-spun microribbons can be tuned by varying the ratios of PEG components with different end-group chemistry. The biochemical cue on microribbons was subsequently introduced by covalently linking biochemical ligands of choice, which supports spatial patterning of multiple bioactive ligands in 3D to mimic tissue zonal organization. As a proof-of-principal study, we encapsulated human adipose-derived stromal cells (hADSCs) in 3D scaffolds with decoupled niche properties formed using PEG-based microribbons. A total of 8 groups were examined with independently tunable biochemical cue (CGRDS vs. cysteine), stiffness (6 kPa vs. 80 kPa) and macroporosity (5% vs. 3.8% w/w). Outcomes were examined by cell morphology and cell proliferation using confocal microscope imaging and biochemical assays.

To synthesize PEG-based microribbons with tunable biochemical and mechanical properties, we selected 8-arm PEG with n-hydroxysuccinimide end groups (PEG-NHS$_8$, MW≈10 kDa) as the starting materials. To tune the microribbon stiffness, half of the NHS-end groups on 8-arm PEG were substituted by either hydroxyl group (—OH) or methacrylate (-MA) moieties to produce PEG-NHS$_4$—OH$_4$ and PEG-NHS$_4$-MA$_4$, respectively. By varying the ratio of PEG-NHS$_4$—OH$_4$ and PEG-NHS$_4$-MA$_4$ in the precursor solution for wet-spinning, we can obtain microribbons with different stiffness. Specifically, increasing the ratio of PEG-NHS$_4$-MA$_4$ increases the stiffness of the resulting microribbons, as the methacrylate end group (MA$_4$) allows further crosslinking of the microribbons during the later photopolymerization process for 3D scaffold formation. The wet-spun PEG microribbons are bioinert, which provides a blank slate for biochemical modification. To introduce biochemical ligands onto microribbon surface, the microribbons with varying stiffness can be subsequently coated with PEG-NHS$_4$-Mal$_4$ precursor, which was synthesized by substituting half of the NHS-end groups of PEG-NHS$_8$ with maleimide (Mal) end groups. We chose the maleimide cross-linking chemistry for incorporating biochemical cues given its mild and rapid reaction, demonstrated cell compatibility, and ease for incorporating of thiolated proteins or peptides through thiol-ene coupling[25]. The wet-spinning process to fabricate PEG-based microribbons is outlined in. The PEG precursors (PEG-NHS$_4$—OH$_4$ and PEG-NHS$_4$-MA$_4$) were dissolved in acetonitrile and mixed at varying ratio to control the stiffness of resulting microribbons, and then injected from a syringe pump into tris(2-aminoethyl) amine (TAEA) bath under constant stirring (125 rpm). Under the shear-force of the stirring flow, the TAEA crosslinked the PEG precursor solution into microribbon-shaped hydrogels. By adjusting the feeding-rate of precursors from 2.5 to 5.0 mL/hr, the width of the microribbons can be tuned from 50 μm to 200 μm. The as-spun microribbons were then coated with PEG-NHS$_4$-Mal$_4$ for biochemical tunability and additional PEG-NHS$_4$-MA$_4$ to allow intercrosslinking among microribbons to form 3D macroporous scaffolds. For direct cell encapsulation, PEG-based microribbons were suspended in PBS, mixed with cells at desired cell-density, and photocrosslinked (365 nm, 2.5 mW/cm$^2$, 4 minutes) into cell-laden, macroporous scaffolds in the presence of photoinitiator phenyl-2,4,6-trimethylbenzoyl-phosphinate[26]. Scanning electron microscope (SEM) imaging showed that the crosslinked PEG-microribbons resembled a "highway system" with interconnected macroporosity throughout the whole scaffold. The level of macroporosity can be tuned by varying the density or width of PEG-microribbons. For example, increasing the microribbon density from 2% to 5% (w/w) decreased the sizes of macropores from 300-500 μm to 50-100 μm. Similar results may also be achieved by increasing the width of microribbon blocks from 50-100 μm to 100-200 μm. Macroporosity also affects the average surface curvatures for cell adhesion, which may influence cell fate by modulating cytoskeleton tension in 3D[14, 15, 27].

Increasing evidence has highlighted the importance of matrix stiffness in dictating cell fates such as stem cell differentiation and self-renewal[28-30]. One advantage of our microribbon-based scaffold design is the ability to decouple microscopic stiffness that cells sense from the macroscopic stiffness of the bulk scaffold. Specifically, the microscopic matrix stiffness that cells sense is dictated by the stiffness of each individual microribbon, whereas the macroscopic stiffness of the bulk scaffold can be controlled by varying the density of microribbon building blocks. In our design, we can tune the stiffness of individual PEG-based microribbons by varying the ratio between PEG-NHS$_4$-MA$_4$ and PEG-NHS$_4$—OH$_4$ during wet spinning. Specifically, by increasing the proportion of PEG-NHS$_4$-MA$_4$ from 0 to 100%, we increased the stiffness of PEG-microribbons from 6.4±0.7 kPa to 76.9±18.3 kPa, a range that has been shown to induce mesenchymal stem cell (MSC) differentiation toward multiple lineages such as muscles, cartilages and bones[29]. The macroscopic mechanical property of the crosslinked microribbon scaffold can be tuned by varying the stiffness and density of microribbon building blocks. Increasing the density of soft (~6 kPa) microribbons from 3.75 to 5% (w/w) increased the scaffold stiffness from 2.6±0.2 to 8.2±0.7 kPa, and increasing the density of stiff (~80 kPa) microribbons from 3.75 to 5% (w/w) increased the scaffold stiffness from 9.9±1.1 to 22.6±1.0 kPa.

The ability of scaffold to sustain compression is an important aspect for engineering load-bearing tissues such as cartilage and bone, but is often hard to achieve using conventional hydrogels. We specifically chose the geometry of microribbons, which resembled thin cantilever beams that transmit mechanical loading easily by bending deformation[31]. Microribbons are inherently flexible due to the low area moment of inertia rendered by the microribbon morphology[31]:

$$J_{ww} = \frac{A^2}{12}\left(\frac{t}{w}\right) \quad (1)$$

where A represents the microribbon's cross-sectional area, w and t the width and thickness of microribbons, and $J_{ww}$ the microribbons' area moment of inertia, which quantifies the resistance to bending deformation of microribbon. The flat cross section of microribbons produced small $J_{ww}$, which renders high flexibility of the resulting microribbons and scaffolds.

We have reported recently that 3D scaffolds formed using gelatin microribbons demonstrated superior flexibility and mechanical stability compared to scaffolds formed using gelatin microfibers with round cross-sections[13]. We performed mechanical testing on scaffolds formed using PEG-based microribbons, and showed the resulting scaffolds could sustain 40%, 1 Hz cyclic compression without failing using 5% (w/w) stiff PEG-microribbon modules.

The biochemical cue that cells would sense in a microribbon-based scaffold is determined by the surface chemistry of PEG-based microribbons. To examine the efficacy of biochemical ligand incorporation, PEG-based microribbons consisting of the "stiff" precursor (PEG-NHS4-MA4) and maleimide coating were treated with cell adhesive peptide CRGDS, in which the cysteine (Cys) end-group can be covalently linked with maleimide via thiol-ene addition. Microribbons coated with Cys were included as a control. We then seeded human adipose-derived stromal cells (hADSCs) on top of the resulting microribbon-scaffolds and examined cell morphology using fluorescence staining of microtubules and actin filaments. We observed extensive hADSC spreading on CRGDS-treated microribbons, whereas cells remained spherical and form small cell clusters on Cys-treated microribbons. Histogram analyses of cell area (n>300) confirmed that CRGDS-treated microribbons significantly enhanced cell spreading in comparison with Cys-treated microribbons. These results confirm that our method allows effective incorporation of biochemical cues onto microribbon surface with retained biological activity. As most tissue regeneration often requires the synergy of multiple types of biochemical ligands, our PEG-based microribbons possessed the biochemical tunability to incorporate a variety of biomolecules including peptides, proteins or glycoaminoglycans to promote desirable tissue formation. We also assessed the effects of varying microribbon stiffness on cell morphology by plating hADSCs on scaffolds fabricated from either soft (~6 kPa) or stiff (~80 kPa) microribbons functionalized with CRGDS. Immunostaining of actin filaments (green) and α-tubulin (red)

showed that both groups supported cell adhesion and spreading by day 3, with more extensive cell-spreading observed on stiff microribbons in comparison with the soft microribbons.

We next explored the potential to spatially pattern different biochemical cues in microribbon-based scaffolds. This is particularly useful for recreating zonal organization for tissue regeneration or for studying cell responses to spatially-patterned biochemical cues. As a proof-of-principle study, we used fluorescein (green) or rhodamine (red)-labeled fibrinogen as two model biomolecules to visualize the spatial distribution of biochemical cues in the scaffold. Fluorescence imaging demonstrated that we can present one type of biochemical cue at a time or co-localizing two biochemical ligands simultaneously, which would be useful in scenarios where co-localization of multiple biochemical ligands are needed to activate desirable cellular responses. Microribbons with distinctive biochemical cues can be spatially patterned to mimic the zonal organization of native tissues, such as the laminar organization of cartilage [32]. While we demonstrated a bi-layered patterned structure as an example, we disclose and enable the easy adaption of our platform to create more complex patterns that mimic zonal organization of specific tissue types.

Macroporosity in tissue engineering scaffolds is desirable and supports tissue regeneration by facilitating nutrient diffusion, cell proliferation, ECM production and faster blood vessel ingrowth [11]. To demonstrate the effects of tuning macroporosity in our microribbon-based scaffolds on cellular response, hADSC were encapsulated in RGD functionalized, microribbon-based scaffolds with two different microribbon density (3.8 or 5.0% w/w). Increasing microribbon density from 3.8% to 5% (w/w) resulted in a decrease in the size of macropores in the scaffolds. Confocal microscopy showed that the hADSCs cultured within larger macropores exhibited cell spreading mostly on individual microribbons, which is more comparable to 2D culture. In contrast, hADSCs cultured within smaller macropores formed contacts with multiple microribbons at the same time, which resembled a 3D culture and demonstrated more direct cell-cell contacts (Animated confocal images of hADSCs-laden scaffolds with 3.8 or 5.0% microribbon-densities were recorded).

One unique advantage of the PEG-based, microribbon-like hydrogels is that they allow independently tunable niche properties of the resulting macroporous scaffolds. As a proof-of-principle study, hADSCs were encapsulated in eight groups of microribbons-based scaffolds with varying biochemical cues (CRGDS vs. Cys), microribbon stiffness (6 kPa vs. 80 kPa) and macroporosity by varying microribbon densities (3.8% vs. 5.0% w/w). Cell proliferation inside different scaffolds was quantified on day 6 using a WST-8 assay. As expected, all scaffolds coated with CRGDS resulted in 2-9 fold higher cell proliferation compared to their respective controls groups coated with Cys. The highest cell proliferation was observed in RGD-containing, softer microribbon-based scaffolds (6 kPa) with smaller macropores (5%). At the higher microribbon density (5%, CRGDS), soft microribbons resulted in 126% more cell proliferation compared to stiff microribbons (80 kPa) ($p<0.001$). This might be contributed by the larger surface area for cell adhesion and proliferation in scaffolds with higher microribbon density. Interestingly, varying microribbon stiffness did not markedly change cell proliferation in microribbon-based scaffolds with larger macroporosity (3.8%).

In summary, here we report the design and synthesis of PEG-based, crosslinkable microribbons as building blocks for fabricating cell-laden, macroporous scaffold with independently tunable niche properties including biochemical, mechanical and topographical cues. Such biomaterials platforms provide a valuable tool to facilitate the analyses of how the interaction of multi-factorial niche signaling influences cell fate in 3D. Meanwhile, it may also be used to promote desirable cellular process and tissue formation through fine tuning of scaffold cues to identify optimal scaffold compositions. The unique geometry of microribbons renders the resulting scaffold with flexibility to absorb cyclic stress, which are particularly useful for engineering tissues types where flexibility is desirable, such as musculoskeletal tissues or cardiovascular tissues. Finally, our platform also supports facile spatial patterning of biochemical cues in 3D, which can facilitate recreating the zonal organization observed in many tissue types.

REFERENCES

[1] D. T. Scadden, *Nature.* 2006, 441, 1075-9.
[2] G. H. Underhill, S. N. Bhatia, *Curr Opin Chem. Biol.* 2007, 11, 357-66.
[3] J. A. Burdick, G. Vunjak-Novakovic, *Tissue Eng Part A.* 2009, 15, 205-19.
[4] E. Cukierman, R. Pankov, D. R. Stevens, K. M. Yamada, *Science.* 2001, 294, 1708-12.
[5] C. A. DeForest, B. D. Polizzotti, K. S. Anseth, *Nat. Mater.* 2009, 8, 659-64.
[6] C. A. Deforest, E. A. Sims, K. S. Anseth, *Chemistry of materials: a publication of the American Chemical Society.* 2010, 22, 4783-90.
[7] M. Nii, J. H. Lai, M. Keeney, L. H. Han, A. Behn, G. Imanbayev, F. Yang, *Acta Biomater.* 2013, 9, 5475-83.
[8] D. S. Benoit, M. P. Schwartz, A. R. Durney, K. S. Anseth, *Nat. Mater.* 2008, 7, 816-23.
[9] M. P. Lutolf, J. A. Hubbell, *Nat. Biotechnol.* 2005, 23, 47-55.
[10] E. S. Place, N. D. Evans, M. M. Stevens, *Nat. Mater.* 2009, 8, 457-70.
[11] S. J. Hollister, *Nat. Mater.* 2005, 4, 518-24.
[12] L. H. Han, J. H. Lai, S. Yu, F. Yang, *Biomaterials.* 2013, 34, 4251-8.
[13] L.-H. Han, S. Yu, T. Wang, A. W. Behn, F. Yang, *Adv Funct Mater.* 2013, 23, 346-58.
[14] M. Rumpler, A. Woesz, J. W. C. Dunlop, D. J. T. van, P. Fratzl, *J R Soc Interface.* 2008, 5, 1173-80.
[15] J. A. Sanz-Herrera, P. Moreo, J. M. Garcia-Aznar, M. Doblare, *Biomaterials.* 2009, 30, 6674-86.
[16] M. Jamal, N. Bassik, J.-H. Cho, C. L. Randall, D. H. Gracias, *Biomaterials.* 2010, 31, 1683-90.
[17] D. Y. Fozdar, P. Soman, J. W. Lee, L. H. Han, S. Chen, *Adv Funct Mater.* 2011, 21, 2712-20.
[18] J. Rnjak-Kovacina, S. G. Wise, Z. Li, P. K. M. Maitz, C. J. Young, Y. Wang, A. S. Weiss, *Biomaterials.* 2011, 32, 6729-36.
[19] J. Xiao, H. Duan, Z. Liu, Z. Wu, Y. Lan, W. Zhang, C. Li, F. Chen, Q. Zhou, X. Wang, J. Huang, Z. Wang, *Biomaterials.* 2011, 32, 6962-71.
[20] M. J. Mondrinos, R. Dembzynski, L. Lu, V. K. Byrapogu, D. M. Wootton, P. I. Lelkes, J. Zhou, *Biomaterials.* 2006, 27, 4399-408.
[21] S. Y. Chew, R. Mi, A. Hoke, K. W. Leong, *Adv Funct Mater.* 2007, 17, 1288-96.
[22] Y. Hong, J. Guan, K. L. Fujimoto, R. Hashizume, A. L. Pelinescu, W. R. Wagner, *Biomaterials.* 2010, 31, 4249-58.
[23] A. P. Zhang, X. Qu, P. Soman, K. C. Hribar, J. W. Lee, S. Chen, S. He, *Adv Mater.* 2012, 24, 4266-70.
[24] J. Zhu, *Biomaterials.* 2010, 31, 4639-56.

[25] E. A. Phelps, N. O. Enemchukwu, V. F. Fiore, J. C. Sy, N. Murthy, T. A. Sulchek, T. H. Barker, A. J. Garcia, *Adv Mater.* 2012, 24, 64-70, 2.

[26] B. D. Fairbanks, M. P. Schwartz, C. N. Bowman, K. S. Anseth, *Biomaterials.* 2009, 30, 6702-7.

[27] S, Nuernberger, N. Cyran, C. Albrecht, H. Redl, V. Vecsei, S. Marlovits, *Biomaterials.* 2010, 32, 1032-40.

[28] D. E. Discher, P. Janmey, Y. L. Wang, *Science.* 2005, 310, 1139-43.

[29] S. S. Adam J. Engler, H. Lee Sweeney, Dennis E Discher, *Cell.* 2006, 126, 677-89.

[30] P. M. Gilbert, K. L. Havenstrite, K. E. Magnusson, A. Sacco, N. A. Leonardi, P. Kraft, N. K. Nguyen, S. Thrun, M. P. Lutolf, H. M. Blau, *Science.* 2010, 329, 1078-81.

[31] W. D. Callister. Materials Science And Engineering: An Introduction: John Wiley & Sons; 2007.

[32] T. A. Einhorn, J. A. Buckwalter, R. J. O'Keefe, A.A.o.O, Surgeons. Orthopaedic basic science: foundations of clinical practice: American Academy of Orthopaedic Surgeons; 2007.

Materials and Methods

Materials

Tripentearythritol functionalized by eight poly (ethylene glycol) succinimidyl succinamide groups (PEG-NHS$_8$, MW=10,000) was purchased from Jenkem Technology (Texas, USA). Peptide Cys-Arg-Gly-Asp-Ser (CRGDS) was synthesized by Bio Basic Inc (Ontario, Canada). 2-aminoethyl methacrylate hydrochloride (AEMA), N,N-diisopropylethylamine, 5-amino-1-pentanol (APOH), N-(2-aminoethyl) maleimide trifluoroacetate salt (AEMal), tris(2-aminoethyl) amine (TAEA), L-cysteine, 2,4,6-trimethylbenzoyl chloride, dimethylphenylphosphonite, 5-carboxy-tetramethylrhodamine n-succinimidyl ester (rhodamine-NHS), anhydrous acetonitrile, and anhydrous isopropanol (IPA) were purchased from Sigma-Aldrich (Missouri, USA). 5(6)-carboxyfluorescein n-hydroxysuccinimide (fluorescein-NHS) was purchased from Thermo Scientific (Illinois, USA). AEMA was recrystallized in acetonitrile before use. All other chemicals were used as received.

Synthesizing the Precursors for Microribbons

To synthesize precursor PEG-NHS$_4$-MA$_4$, PEG-NHS$_8$ (1 g, 0.1 mmol) was dissolved in 2 mL anhydrous acetonitrile, AEMA (66.3 mg, 0.4 mmol) and N,N-diisopropylethylamine (67.7 µL, 0.4 mmol) was dissolved in 1 mL anhydrous acetonitrile. The two solutions were then mixed and stirred vigorously for 24 h at RT. To synthesize precursor PEG-NHS$_4$-Mal$_4$, PEG-NHS$_8$ (1 g, 0.1 mmol) was dissolved in 2 mL anhydrous acetonitrile, AEMal (203.3 mg, 0.8 mmol) and N,N-diisopropylethylamine (30.5 µL, 0.18 mmol) were dissolved in 1 mL anhydrous acetonitrile. The two solutions were mixed and stirred vigorously for 24 h at RT. To synthesize precursor PEG-NHS$_4$—OH$_4$, PEG-NHS$_8$ (1 g, 0.1 mmol) was dissolved in 2 mL anhydrous acetonitrile (2 mL), APOH (43.5 µL, 0.4 mmol) was dissolved in 1 mL anhydrous acetonitrile, and the two solutions were mixed and stirred vigorously for 24 h at RT. All products were precipitated twice in anhydrous IPA (50 mL), dried under vacuum, and stored at −20° C. before use.

Producing PEG Microribbons by Wet-Spinning

The precursors (PEG-NHS$_4$-MA$_4$, PEG-NHS$_4$—OH$_4$ and PEG-NHS$_4$-Mal$_4$) were dissolved in acetonitrile to reach a concentration of 30% (wt/v). IPA (1 L) and TAEA (30 mL) were mixed in a glass beaker and stirred at 125 rpm with a disk-shaped spinner mounted on the bottom. Four steel wires were mounted on the spinner to collect as-formed microribbons. The solution of PEG-NHS$_4$—OH$_4$ or PEG-NHS$_4$-MA$_4$ (2 mL) was injected perpendicularly into the tank at either 2.5 or 5 mL/hr through a blunt-head needle (30 G) to form continuous microribbons. The as-formed microribbons were rinsed by methanol (40 mL, 5 min) and subsequently by ethanol (40 mL, 5 min per wash, four times).

The microribbons produced from 2 mL precursor solution were stirred for 3 h at RT in 40 mL ethanol with 0.04 wt % PEG-NHS$_4$-Mal$_4$ and 0.04 wt % PEG-NHS$_4$-MA$_4$, rinsed by DI water (40 mL, 37° C., 10 mins, eight times), concentrated by centrifuge, and were kept hydrated in PBS. When constructing scaffolds, microribbon density in the macroporous scaffolds was defined as dry weight over wet weight (w/w).

Preparing Microribbons with Varying Biochemical Ligands

Microribbons (50 mg in dry weight) were stirred in 5 mL PBS at 37.5° C. for 5 h with either L-cysteine (Cys) or CRGDS (80 mM). The modified microribbons were rinse at 37.5° C. by PBS (50 mL, 30 mins, 8 times) and stored at 4° C. before use.

Modifying the Microribbons by Fluorescence-Labeled Fibrinogen

To synthesize fluorescence-labeled fibrinogen, fibrinogen (250 mg) was dissolved in 8M urea in PBS (25 mL), and then mixed with fluorescein-NHS or rhodamine-NHS (0.1 mmol in 100 µL chloroform). The mixture was stirred for 2 h at RT, then purified in 8M urea in PBS by centrifugal filtration with 10 k MWCO. Microribbons (50 mg in dry-weight) were stirred in PBS (5 mL) at 37.5° C. for 3 h in 8M urea with fluorescein- or rhodamine-labeled fibrinogen (50 mg), rinsed by 8M urea in PBS (50 mL, 30 min, 8 times) and stored at 4° C. before use.

Synthesizing Photoinitiator LAP

Photoinitiator lithium phenyl-2,4,6-trimethylbenzoylphosphinate (LAP) was prepared according to existing protocol [22]. In brief, 2,4,6-trimethylbenzoyl chloride (3.2 g) was added by drops to dimethylphenylphosphonite (3.0 g) under argon pressure and was stirred for 18 hrs. The mixture was then heated to 50° C., and added by lithium bromide (6.1 g) in 2-butanone (100 mL). After 10 min, the mixture was cooled to RT, allowed to rest for four hours, and filtered to collect crude product. The product was washed 3 times with 2-butanone and dried under vacuum.

Fabricating Macroporous Scaffolds

To prepare 3D scaffolds, PEG microribbons were concentrated in PBS by different densities (2%, 4%, and 5% w/w), added with LAP initiator (0.05% w/v), loaded into cylindrical molds (diameter: 5.6 mm; height: 3 mm). Upon exposure to light (365 nm, 3 mW/cm$^2$, 5 min), microribbons further crosslink to form 3D macroporous scaffolds. The resulting scaffolds were incubated in PBS at 37° C. overnight before subsequent characterizations. To prepare microribbon sheets for culturing cells on 2D, microribbons with varying rigidity and biochemical ligands (CRGDS or Cys) were suspended in PBS (5% w/w), pressed to form 200 µm-thick layers at the bottoms of a 96-well plate, and then crosslinked by UV light (3 mW/cm$^2$, 5 min). The resulting microribbon sheets were rinsed twice by PBS before cell seeding.

Scanning Electron Microscopy

The morphology of hydrated microribbon-based scaffolds was assessed using a Hitachi S-3400N variable pressure scanning electron microscope (VP-SEM). Before being loaded to the chamber of SEM, samples were rinsed with PBS and dissected by razor blade to expose internal macropores. The hydrated samples were gradually cooled from room temperature to −25° C. as the chamber pressure reduced from 1 atm to 50 Pa, following a P/T curve at which water stays liquid phase. The samples were imaged under the electron beam intensity at 15 kV and working distance around 7 mm.

Isolation and Culture of Human Adipose-Derived Stromal Cells

Human adipose-derived stromal cells (hADSCs) were isolated from lipoaspirated human fat tissue as previously described [29]. All the procedure involving human tissue has been approved by the Stanford Institutional Review Board. The fat Tissues were washed 2-3 times with PBS and digested at 37° C. for 30 min with Blendzyme 3 (Roche Diagnostics, Indianapolis, Ind.) (0.5 U/ml). Enzyme activity was neutralized with Dulbecco's Modified Eagle Medium (DMEM), containing fetal bovine serum (FBS, Invitrogen) (10% v/v) and antibiotic Penicillin/Streptomycin (P/S) solution (1% v/v). The cells were then filtered through a 70 μm cell strainer to remove cellular debris, counted and seeded onto tissue culture flasks. Following the initial 48 h of incubation at 37° C. and 5% $CO_2$, cells were washed with PBS and expanded in growth medium containing DMEM with 10% FBS, 1% P/S and basic fibroblast growth factor (bFGF, 10 ng/ml) (Pepro-Tech, Rocky Hill, N.J.). Cells were passaged upon 85-90% confluence and passage 4 cells were used for all experiments.

Cell Spreading on PEG-Based Microribbon Sheets

The microribbons with varying biochemical cues or stiffness were fabricated into 200 μm-thick sheets as described earlier, which were then used as substrates for seeding hADSCs at a density of 20,000 cells per well. On day 2, the hADSCs were stained using LIVE/DEAD® Viability/Cytotoxicity Kit for mammalian cells (Invitrogen). Cell morphology on the microribbons were imaged using fluorescence microscopy and analyzed using Image J (n=300/group). Cell-spreading was quantified by the pixel areas of hADSCs. To examine the morphology of cytoskeletons, the samples from each group were fixed for 15 minutes in 4% paraformaldehyde and washed three times by PBS, cell membranes were permeablized using Triton-X (0.1% in PBS), and actin filaments were stained overnight at 4° C. using phalloidin-TRITC (5 μg/mL in PBS). The samples were then treated by blocking buffer consisting of 2% goat serum and 3% BSA in PBS, followed by incubation overnight at 4° C. in mouse monoclonal antibody to α-tubulin (Alexa Fluor 488 mouse anti-α-tubulin, EMD Millipore). Nuclei were counterstained with Hoechst stain (Life Technology) and images were taken with a Zeiss fluorescence microscope.

Cell Proliferation in Crosslinked Microribbon-Based PEG Scaffolds

Trypsinized hADSCs were gently suspended with PEG-microribbons at cell density of 2 million per mL. The microribbons were molded between two glass slides (with gap of 1 mm in between) and exposed to the source of UV light (365 nm, 4 mW $cm^{-2}$, 5 min), forming 1 mm-thick, cell-laden scaffolds. Following the initial 12 hours of incubation (37° C., 5% $CO_2$), cylindrical samples (5 mm in diameter) were cut from the cell-laden scaffolds and incubated in 48-well plate (n=6 per group). Cell proliferation of hADSCs was quantified on day 0, 3, and 10 using WST-8 proliferation kit (Cayman Chemical, Michigan, USA) following manufacturer's protocol. To examine cell morphology on scaffolds, samples from each group were collected on day 3 and 10, fixed in 4% paraformaldehyde at 37° C. for 30 min, and stained for actin filaments, microtubules and nuclei following the aforementioned procedures. Z-stack images of cytoskeletons were taken by using a Leica SP5 confocal microscope. The cytoskeletal structures in 3D scaffolds were reconstructed using ImageJ.

Mechanical Testing

To quantify the bulk mechanical property of microribbon-based scaffolds, Unconfined compression tests were conducted using an Instron 5944 materials testing system (Instron Corporation, Norwood, Mass.) fitted with a 10 N load cell (Interface Inc., Scottsdale, Ariz.). Custom-made aluminum compression platens lined with PTFE were used to minimize friction. All tests were conducted in PBS solution at RT. Before each test, the sample's diameter and thickness were measured using digital calipers. A preload of approximately 2 mN was applied to ensure the scaffold surface was in full contact with the upper platen. To measure the compressive modulus, the upper platen was lowered at a rate of 1% strain per second to a maximum strain of 30%. Load and displacement data were recorded at 100 Hz. Stress vs. strain curves were created and curve fit using a third order polynomial equation. The compressive modulus of scaffold was determined from the curve fit equation at strain values from 0 to 10%.

To quantify the microscopic stiffness of microribbons, bulk samples of crosslinked precursors were prepared. Solution of microribbon precursor (1 mL, 30 wt % PEG-4NHS-4MA or PEG-4NHS-40H in acetonitrile) was crosslinked by TAEA (20 μL) for 24 hours in a sealed cylinder (5.6 mm in diameter), cut into 3 mm-thick samples, incubated overnight at 37.5° C. in PBS with 0.05% LAP, exposed to UV light for secondary crosslinking (365 nm, 4 mW $cm^{-2}$, 5 min), and incubated overnight again at 37° C. in PBS before mechanical testing.

Statistical Analysis

All data were expressed as mean±standard error and statistical significance was determined by analysis of variance using student's t-test with equal variance. p values (two-tails) of less than 0.05 were considered statistically significant, and p values less than 0.005 were considered statistically highly significant.

III. Additional Results

We have expanded the set of exemplified microribbon materials to include multiple poly(ethylene glycol)-based chemicals to achieve a higher range of ECM properties. The stiffness and surface chemical of microribbons are demonstrably independently tunable, which facilitates the optimizing of scaffold properties for desirable cell fate and tissue formation, which are sensitive to ECM stiffness, biochemical property, and macroporosity.

We have also successfully performed translational studies, including a mice cranial defect model, in which we have implanted stem-cell-laden, microribbon-based scaffolds to the defects at mice skull and monitored the bone regrowth. For example, we demonstrated bone regeneration using micro-morphology of two different scaffolds. At 15% w/w, the gelatin-based microribbon form macroporous scaffolds, which provide cell-size (about 10 microns) porosity to facilitate cell migration, proliferation and production of extracellular matrix materials. In contrast, the hydrogel from by the same amount of gelatin (15% w/w) gives very limited porosity, and cells have limited space to performed the activity leading to wound healing.

48 hours after encapsulation, mouse adipose derived stem cells (mADSCs) in μ-ribbons spread vigorously, as the cells in hydrogel remained roundish.

Four surgical groups were defined: Group 1: gelatin hydrogel, 15% w/w, no cells; Group 2: μ-ribbons, 15% w/w mADSCs, 10M/mL; Group 3: μ-ribbons, 15% w/w, no cells; Group 4: gelatin hydrogel, 15% w/w, mADSCs, 10M/mL. A 4 mm defect was created on the right parietal bone of each mouse. Microribbon-based and hydrogel-based scaffolds (D: 2 mm, t: 250 μm) with mADSCs were implanted to the defect. Bioluminescent imaging (BLI) was used to quantify the proliferation/viability of mADSCs on a weekly basis.

The BLI result show that, compared to hydrogel containing limited macroporosity, the microribbons formed by the same material (gelatin) support cell survival in the bone defect at significantly higher level. Our results are consistent with the microribbons providing macropores to support the nutrient diffusion around the cells, and/or providing better cell-spreading, which normally encourages cell survival.

We also demonstrated a rat cartilage model which confirms the beneficial effect of microribbons on healing cartilage defects.

We also demonstrated additional methods to fabricate different shapes of microscaled hydrogels for making macroporous scaffols, including inkjet-printing as an additional fabrication method to prepare the building blocks for the macroporous scaffold. Biomaterials are loaded into different inkjet cartridges, and sprayed onto a matrix to produce in different shapes the elements for crosslinking and making macroporous scaffolds. Such inkjet printing has become a commonly used tool for fast fabrication of small blocks of specific shapes from many different materials, including polymers and inorganic materials.

What is claimed is:

1. A method of making microribbons, the method comprising:
wet-spinning a solution comprising a first multi-armed synthetic polymer comprising N-hydroxysuccinimide ester ("NHS ester") end groups and methacrylate ("MA") end groups and a second multi-armed synthetic polymer comprising NHS ester end groups and hydroxyl (OH) end groups into a bath comprising an anti-solvent and tris(2-aminoethyl)amine ("TAEA"), whereby the shear force of the stirring flow initiates a crosslinking reaction between various amine groups of the TAEA and various NHS ester end groups of the first multi-armed synthetic polymer and the second multi-armed synthetic polymer, yielding the microribbons.

2. The method of claim 1, wherein the molecular structure of the first multi-armed synthetic polymer includes a polymer selected from the group consisting of poly(ethylene glycol), poly(lactic-co-glycolic acid), poly(glycolic acid), poly(lactic acid), polycaprolactone, and poly(methyl methacrylate).

3. The method of claim 1, wherein the molecular structure of the second multi-armed synthetic polymer includes a polymer selected from the group consisting of poly(ethylene glycol), poly(lactic-co-glycolic acid), poly(glycolic acid), poly(lactic acid), polycaprolactone, and poly(methyl methacrylate).

4. The method of claim 2, wherein the molecular structure of the second multi-armed synthetic polymer includes a polymer selected from the group consisting of poly(ethylene glycol), poly(lactic-co-glycolic acid), poly(glycolic acid), poly(lactic acid), polycaprolactone, and poly(methyl methacrylate).

5. The method of claim 1, wherein the first multi-armed synthetic polymer is an eight-armed poly(ethylene glycol) ("PEG") having the following formula: PEG-(NHS ester)$_4$-(MA)$_4$.

6. The method of claim 1, wherein the second multi-armed synthetic polymer is an eight-armed poly(ethylene glycol) ("PEG") having the following formula: PEG-(NHS ester)$_4$-(OH)$_4$.

7. The method of claim 5, wherein the second multi-armed synthetic polymer is an eight-armed poly(ethylene glycol) ("PEG") having the following formula: PEG-(NHS ester)$_4$-(OH)$_4$.

8. A method of making a three-dimensional (3D) tissue engineering scaffold, the method comprising:
wet-spinning a solution comprising a first multi-armed synthetic polymer comprising N-hydroxysuccinimide ester ("NHS ester") end groups and methacrylate ("MA") end groups and a second multi-armed synthetic polymer comprising NHS ester end groups and hydroxyl (OH) end groups into a bath comprising an anti-solvent and tris(2-aminoethyl)amine ("TAEA"), whereby the shear force of the stirring flow initiates a crosslinking reaction between various amine groups of the TAEA and various NHS ester end groups of the first multi-armed synthetic polymer and the second multi-armed synthetic polymer, yielding microribbons;
suspending the microribbons in a liquid;
adding a photoinitiator to the liquid;
irradiating the liquid with light sufficient to initiate a photocrosslinking reaction between various MA end groups, thereby yielding the 3D tissue engineering scaffold.

9. The method of claim 8, further comprising suspending living cells in the liquid, before irradiating the liquid with light sufficient to initiate the photocrosslinking reaction.

10. The method of claim 9, wherein the living cells are stem cells.

11. The method of claim 8, wherein the liquid is phosphate-buffered saline.

12. The method of claim 8, wherein the photoinitiator is lithium phenyl-2,4,6-trimethylbenzoylphosphinate.

13. The method of claim 8, further comprising coating the microribbons with an additional amount of the first multi-armed synthetic polymer comprising N-hydroxysuccinimide ester ("NHS ester") end groups and methacrylate ("MA") end groups, before suspending the microribbons in the liquid.

14. The method of claim 8, further comprising coating the microribbons with a third multi-armed synthetic polymer comprising maleimide end groups, before suspending the microribbons in the liquid.

15. The method of claim 14, further comprising covalently bonding molecules of a thiolated bioactive ligand to various maleimide end groups of the coating via thiol-ene addition.

16. The method of claim 15, wherein the thiolated bioactive ligand is a protein or peptide.

17. The method of claim 8, wherein the molecular structure of the first multi-armed synthetic polymer includes a polymer selected from the group consisting of poly(ethylene glycol), poly(lactic-co-glycolic acid), poly(glycolic acid), poly(lactic acid), polycaprolactone, and poly(methyl methacrylate).

18. The method of claim 8, wherein the molecular structure of the second multi-armed synthetic polymer includes a polymer selected from the group consisting of poly(ethylene glycol), poly(lactic-co-glycolic acid), poly(glycolic acid), poly(lactic acid), polycaprolactone, and poly(methyl methacrylate).

19. The method of claim 8, wherein the first multi-armed synthetic polymer is an eight-armed poly(ethylene glycol) ("PEG") having the following formula: PEG-(NHS ester)$_4$-(MA)$_4$.

20. The method of claim 8, wherein the second multi-armed synthetic polymer is an eight-armed poly(ethylene glycol) ("PEG") having the following formula: PEG-(NHS ester)$_4$-(OH)$_4$.

* * * * *